US011963712B2

(12) United States Patent
De Marchena

(10) Patent No.: US 11,963,712 B2
(45) Date of Patent: Apr. 23, 2024

(54) TRANSAPICAL REMOVAL DEVICE

(71) Applicant: EVALVE, INC., Santa Clara, CA (US)

(72) Inventor: Eduardo De Marchena, Miami, FL (US)

(73) Assignee: Evalve, Inc., Santa Clara, CA (US)

(*) Notice: Subject to any disclaimer, the term of this patent is extended or adjusted under 35 U.S.C. 154(b) by 1015 days.

(21) Appl. No.: 16/311,529

(22) PCT Filed: Jun. 20, 2017

(86) PCT No.: PCT/US2017/038309
§ 371 (c)(1),
(2) Date: Dec. 19, 2018

(87) PCT Pub. No.: WO2017/223073
PCT Pub. Date: Dec. 28, 2017

(65) Prior Publication Data
US 2019/0183571 A1 Jun. 20, 2019

Related U.S. Application Data

(60) Provisional application No. 62/352,235, filed on Jun. 20, 2016.

(51) Int. Cl.
A61B 18/12 (2006.01)
A61B 17/128 (2006.01)
(Continued)

(52) U.S. Cl.
CPC ...... *A61B 18/1492* (2013.01); *A61B 17/1285* (2013.01); *A61B 17/22* (2013.01);
(Continued)

(58) Field of Classification Search
CPC . A61B 18/1492; A61B 17/1285; A61B 17/22; A61B 17/22031; A61B 17/221;
(Continued)

(56) References Cited

U.S. PATENT DOCUMENTS 3,378,010 A 4/1968 Codling et al.
3,470,875 A 10/1969 Johnson
(Continued)

FOREIGN PATENT DOCUMENTS

CA 2 296 317 C 1/2009
DE 91 00 873 U1 4/1991
(Continued)

OTHER PUBLICATIONS

Extended European search report dated Oct. 10, 2022 in EP 22173362.
(Continued)

*Primary Examiner* — Aaron F Roane
(74) *Attorney, Agent, or Firm* — SLEMAN & LUND LLP

(57) ABSTRACT

A transapical removal device that can be deployed in a catheter procedure to capture for removal or alteration a mitral valve clip or heart tissue, such as the anterior leaflet of the mitral valve, and methods of use are disclosed. The removal device includes a delivery catheter configured to be deployed near a mitral valve using a guide catheter. The delivery catheter has a snare head at the distal end, which assumes a collapsed state during movement of the delivery catheter through the guide catheter and deployed state for capturing a mitral valve clip or anterior leaflet. The snare head has one or more ablation delivery catheters configured to ablate tissue surrounding the pre-positioned mitral valve clip or anterior leaflet. In some arrangements within the scope of the present disclosure, the removal device includes a deployment mechanism for deploying a new transcatheter valve into the mitral valve.

16 Claims, 12 Drawing Sheets

(51) Int. Cl.
*A61B 17/22* (2006.01)
*A61B 17/221* (2006.01)
*A61B 17/32* (2006.01)
*A61B 17/34* (2006.01)
*A61B 17/50* (2006.01)
*A61B 18/02* (2006.01)
*A61B 18/14* (2006.01)
*A61B 18/24* (2006.01)
*A61B 17/00* (2006.01)
*A61B 18/00* (2006.01)

(52) U.S. Cl.
CPC ...... *A61B 17/22031* (2013.01); *A61B 17/221* (2013.01); *A61B 17/32* (2013.01); *A61B 17/34* (2013.01); *A61B 17/50* (2013.01); *A61B 18/02* (2013.01); *A61B 18/1445* (2013.01); *A61B 18/24* (2013.01); *A61B 2017/00243* (2013.01); *A61B 2017/00318* (2013.01); *A61B 2017/00358* (2013.01); *A61B 2017/00876* (2013.01); *A61B 2017/22035* (2013.01); *A61B 2017/22097* (2013.01); *A61B 2017/2215* (2013.01); *A61B 2018/00267* (2013.01); *A61B 2018/00273* (2013.01); *A61B 2018/00369* (2013.01); *A61B 2018/00577* (2013.01); *A61B 2018/0212* (2013.01); *A61B 2018/1226* (2013.01)

(58) Field of Classification Search
CPC ......... A61B 17/32; A61B 17/34; A61B 17/50; A61B 18/02; A61B 18/1445; A61B 18/24; A61B 2017/00243; A61B 2017/00318; A61B 2017/00358; A61B 2017/00876; A61B 2017/22035; A61B 2017/22097; A61B 2017/2215; A61B 2018/00267; A61B 2017/3225; A61B 2018/00273; A61B 2018/00369; A61B 2018/00577; A61B 2018/0212; A61B 2018/1226
USPC ......................................................... 607/119
See application file for complete search history.

(56) References Cited

U.S. PATENT DOCUMENTS

| | | | |
|---|---|---|---|
| 3,874,388 A | 4/1975 | King et al. |
| 4,007,743 A | 2/1977 | Blake |
| 4,055,861 A | 11/1977 | Carpentier et al. |
| 4,312,337 A | 1/1982 | Donohue |
| 4,327,736 A | 5/1982 | Inoue |
| 4,340,091 A | 7/1982 | Skelton et al. |
| 4,646,719 A | 3/1987 | Neuman et al. |
| 4,657,024 A | 4/1987 | Coneys |
| 4,693,248 A | 9/1987 | Failla |
| 4,716,886 A | 1/1988 | Schulman et al. |
| 4,795,458 A | 1/1989 | Regan |
| 4,809,695 A | 3/1989 | Gwathmey et al. |
| 4,930,674 A | 6/1990 | Barak |
| 4,998,917 A | 3/1991 | Gaiser et al. |
| 5,002,562 A | 3/1991 | Oberlander |
| 5,069,679 A | 12/1991 | Taheri |
| 5,071,428 A | 12/1991 | Chin et al. |
| 5,098,440 A | 3/1992 | Hillstead |
| 5,125,895 A | 6/1992 | Buchbinder et al. |
| 5,147,370 A | 9/1992 | McNamara et al. |
| 5,171,259 A | 12/1992 | Inoue |
| 5,217,460 A | 6/1993 | Knoepfler |
| 5,222,963 A | 6/1993 | Brinkerhoff et al. |
| 5,238,002 A | 8/1993 | Devlin et al. |
| 5,271,544 A | 12/1993 | Fox et al. |
| 5,327,905 A | 7/1994 | Avitall |
| 5,330,501 A | 7/1994 | Tovey et al. |
| 5,334,217 A | 8/1994 | Das |
| 5,363,861 A | 11/1994 | Edwards et al. |
| 5,389,077 A | 2/1995 | Melinyshyn et al. |
| 5,403,326 A | 4/1995 | Harrison et al. |
| 5,425,744 A | 6/1995 | Fagan et al. |
| 5,450,860 A | 9/1995 | O'Connor |
| 5,452,837 A | 9/1995 | Williamson, IV et al. |
| 5,456,400 A | 10/1995 | Shichman et al. |
| 5,456,674 A | 10/1995 | Bos et al. |
| 5,478,353 A | 12/1995 | Yoon |
| 5,542,949 A | 8/1996 | Yoon |
| 5,562,678 A | 10/1996 | Booker |
| 5,601,224 A | 2/1997 | Bishop et al. |
| 5,601,574 A | 2/1997 | Stefanchik et al. |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,636,634 A | 6/1997 | Kordis et al. |
| 5,695,504 A | 12/1997 | Gifford, III et al. |
| 5,713,911 A | 2/1998 | Racenet et al. |
| 5,716,417 A | 2/1998 | Girard et al. |
| 5,741,297 A | 4/1998 | Simon |
| 5,755,778 A | 5/1998 | Kleshinski |
| 5,782,239 A | 7/1998 | Webster, Jr. |
| 5,797,960 A | 8/1998 | Stevens et al. |
| 5,810,847 A | 9/1998 | Laufer et al. |
| 5,814,097 A | 9/1998 | Sterman et al. |
| 5,820,630 A | 10/1998 | Lind |
| 5,843,178 A | 12/1998 | Vanney et al. |
| 5,849,019 A | 12/1998 | Yoon |
| 5,855,601 A | 1/1999 | Bessler et al. |
| 5,908,420 A | 6/1999 | Parins et al. |
| 5,976,159 A | 11/1999 | Bolduc et al. |
| 6,015,417 A | 1/2000 | Reynolds, Jr. |
| 6,048,351 A | 4/2000 | Gordon et al. |
| 6,079,414 A | 6/2000 | Roth |
| 6,117,144 A | 9/2000 | Nobles et al. |
| 6,120,496 A | 9/2000 | Whayne et al. |
| 6,139,508 A | 10/2000 | Simpson et al. |
| 6,149,658 A | 11/2000 | Gardiner et al. |
| 6,165,183 A | 12/2000 | Kuehn et al. |
| 6,182,664 B1 | 2/2001 | Cosgrove |
| 6,193,734 B1 | 2/2001 | Bolduc et al. |
| 6,200,315 B1 | 3/2001 | Gaiser et al. |
| 6,217,528 B1 | 4/2001 | Koblish et al. |
| 6,269,819 B1 | 8/2001 | Oz et al. |
| 6,290,674 B1 | 9/2001 | Roue et al. |
| 6,312,447 B1 | 11/2001 | Grimes |
| 6,332,880 B1 | 12/2001 | Yang et al. |
| 6,334,860 B1 | 1/2002 | Dorn |
| 6,346,074 B1 | 2/2002 | Roth |
| 6,419,640 B1 | 7/2002 | Taylor |
| 6,419,696 B1 | 7/2002 | Ortiz et al. |
| 6,461,366 B1 | 10/2002 | Seguin |
| 6,482,224 B1 | 11/2002 | Michler et al. |
| 6,496,420 B2 | 12/2002 | Manning |
| 6,540,719 B2 | 4/2003 | Bigus et al. |
| 6,544,215 B1 | 4/2003 | Bencini et al. |
| 6,551,303 B1 | 4/2003 | Van Tassel et al. |
| 6,575,971 B2 | 6/2003 | Hauck et al. |
| 6,599,311 B1 | 7/2003 | Biggs et al. |
| 6,626,930 B1 | 9/2003 | Allen et al. |
| 6,629,534 B1 | 10/2003 | St. Goar et al. |
| 6,669,687 B1 | 12/2003 | Saadat |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,770,083 B2 | 8/2004 | Seguin |
| 6,797,002 B2 | 9/2004 | Spence et al. |
| 6,837,867 B2 | 1/2005 | Kortelling |
| 6,855,137 B2 | 2/2005 | Bon |
| 6,875,224 B2 | 4/2005 | Grimes |
| 6,908,481 B2 | 6/2005 | Cribier |
| 6,926,730 B1 | 8/2005 | Nguyen et al. |
| 6,932,810 B2 | 8/2005 | Ryan |
| 7,011,669 B2 | 3/2006 | Kimblad |
| 7,101,395 B2 | 9/2006 | Tremulis et al. |

(56) References Cited

U.S. PATENT DOCUMENTS

| | | |
|---|---|---|
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,338,467 B2 | 3/2008 | Lutter |
| 7,556,632 B2 | 7/2009 | Zadno |
| 7,563,267 B2 | 7/2009 | Goldfarb et al. |
| 7,569,062 B1 | 8/2009 | Kuehn et al. |
| 7,604,646 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,736,388 B2 | 6/2010 | Goldfarb et al. |
| 7,811,296 B2 | 10/2010 | Goldfarb et al. |
| 7,972,323 B1 | 7/2011 | Bencini et al. |
| 7,981,139 B2 | 7/2011 | Martin et al. |
| 8,057,493 B2 | 11/2011 | Goldfarb et al. |
| 8,062,313 B2 | 11/2011 | Kimblad |
| 8,118,822 B2 | 2/2012 | Schaller et al. |
| 8,216,230 B2 | 7/2012 | Hauck et al. |
| 8,216,256 B2 | 7/2012 | Raschdorf, Jr. et al. |
| 8,303,608 B2 | 11/2012 | Goldfarb et al. |
| 8,500,761 B2 | 8/2013 | Goldfarb et al. |
| 8,623,077 B2 | 1/2014 | Cohn |
| 8,734,505 B2 | 5/2014 | Goldfarb et al. |
| 8,740,920 B2 | 6/2014 | Goldfarb et al. |
| 8,821,518 B2 | 9/2014 | Saliman et al. |
| 8,870,948 B1 | 10/2014 | Erzberger et al. |
| 9,211,119 B2 | 12/2015 | Hendricksen et al. |
| 9,439,757 B2 | 9/2016 | Wallace et al. |
| 9,510,829 B2 | 12/2016 | Goldfarb et al. |
| 9,770,256 B2 | 9/2017 | Cohen |
| 10,076,415 B1 | 9/2018 | Metchik et al. |
| 10,105,222 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,231,837 B1 | 3/2019 | Metchik et al. |
| 10,238,493 B1 | 3/2019 | Metchik et al. |
| 10,245,144 B1 | 4/2019 | Metchik et al. |
| 10,258,408 B2* | 4/2019 | Fung ............... A61B 18/1492 |
| D847,983 S | 5/2019 | Ho et al. |
| 10,314,586 B2 | 6/2019 | Greenberg et al. |
| 10,413,408 B2 | 9/2019 | Krone et al. |
| 10,470,881 B2 | 11/2019 | Noe et al. |
| 10,507,109 B2 | 12/2019 | Metchik et al. |
| 10,517,726 B2 | 12/2019 | Chau et al. |
| 10,524,792 B2 | 1/2020 | Hernandez et al. |
| 10,595,997 B2 | 3/2020 | Metchik et al. |
| 10,624,664 B2 | 4/2020 | Cohen |
| 10,631,893 B2 | 4/2020 | Drapeau |
| 10,646,342 B1 | 5/2020 | Marr et al. |
| 10,736,632 B2 | 8/2020 | Khairkhahan |
| 10,751,173 B2 | 8/2020 | Morriss et al. |
| 10,779,837 B2 | 9/2020 | Lee et al. |
| D902,403 S | 11/2020 | Marsot et al. |
| 10,856,988 B2 | 12/2020 | McNiven et al. |
| 2002/0013571 A1 | 1/2002 | Goldfarb et al. |
| 2002/0183787 A1 | 12/2002 | Wahr et al. |
| 2003/0069593 A1 | 4/2003 | Tremulis et al. |
| 2003/0167071 A1 | 9/2003 | Martin et al. |
| 2004/0034365 A1 | 2/2004 | Lentz et al. |
| 2004/0044350 A1 | 3/2004 | Martin et al. |
| 2004/0116951 A1 | 6/2004 | Rosengart |
| 2005/0159763 A1 | 7/2005 | Mollenauer et al. |
| 2005/0192633 A1 | 9/2005 | Montpetit |
| 2005/0267493 A1 | 12/2005 | Schreck et al. |
| 2006/0074484 A1 | 4/2006 | Huber |
| 2006/0184198 A1 | 8/2006 | Bales et al. |
| 2007/0038293 A1 | 2/2007 | St. Goar et al. |
| 2007/0213735 A1* | 9/2007 | Saadat ............... A61B 17/1659 606/79 |
| 2008/0009858 A1 | 1/2008 | Rizvi |
| 2008/0097467 A1 | 4/2008 | Gruber et al. |
| 2008/0140189 A1* | 6/2008 | Nguyen ................ A61F 2/2412 623/2.11 |
| 2009/0012538 A1 | 1/2009 | Saliman et al. |
| 2009/0082857 A1 | 3/2009 | Lashinski et al. |
| 2009/0209955 A1 | 8/2009 | Forster |
| 2009/0209991 A1 | 8/2009 | Hinchliffe et al. |
| 2010/0268226 A1* | 10/2010 | Epp .................... A61B 18/1492 606/45 |
| 2011/0009864 A1 | 1/2011 | Bucciaglia et al. |
| 2011/0178366 A1* | 7/2011 | Suzuki ................ A61B 17/221 600/104 |
| 2011/0184405 A1 | 7/2011 | Mueller |
| 2011/0238052 A1 | 9/2011 | Robinson |
| 2012/0022527 A1 | 1/2012 | Woodruff et al. |
| 2013/0197299 A1 | 8/2013 | Chin et al. |
| 2014/0046320 A1* | 2/2014 | Kappel ............... A61B 17/3205 606/49 |
| 2014/0228871 A1 | 8/2014 | Cohen et al. |
| 2015/0238729 A1 | 8/2015 | Jenson et al. |
| 2015/0257883 A1 | 9/2015 | Basude et al. |
| 2017/0042546 A1 | 2/2017 | Goldfarb et al. |
| 2017/0049455 A1 | 2/2017 | Seguin |
| 2017/0100250 A1 | 4/2017 | Marsot et al. |
| 2017/0239048 A1 | 8/2017 | Goldfarb et al. |
| 2017/0265994 A1 | 9/2017 | Krone |
| 2018/0021133 A1 | 1/2018 | Barbarino |
| 2018/0036119 A1 | 2/2018 | Wei et al. |
| 2018/0092661 A1 | 4/2018 | Prabhu |
| 2018/0146964 A1 | 5/2018 | Garcia et al. |
| 2018/0235657 A1 | 8/2018 | Abunassar |
| 2018/0242976 A1 | 8/2018 | Kizuka |
| 2018/0243086 A1 | 8/2018 | Barbarino et al. |
| 2018/0325671 A1 | 11/2018 | Abunassar et al. |
| 2018/0344460 A1 | 12/2018 | Wei |
| 2018/0353181 A1 | 12/2018 | Wei |
| 2018/0360457 A1 | 12/2018 | Ellis et al. |
| 2019/0053803 A1 | 2/2019 | Ketai et al. |
| 2019/0125536 A1 | 5/2019 | Prabhu et al. |
| 2019/0151041 A1 | 5/2019 | Ho et al. |
| 2019/0151089 A1 | 5/2019 | Wei |
| 2019/0159899 A1 | 5/2019 | Marsot et al. |
| 2019/0167197 A1 | 6/2019 | Abunassar et al. |
| 2019/0183571 A1 | 6/2019 | De Marchena |
| 2019/0209293 A1 | 7/2019 | Metchik et al. |
| 2019/0247187 A1 | 8/2019 | Kizuka |
| 2019/0274831 A1 | 9/2019 | Prabhu |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1 | 1/2020 | Dell et al. |
| 2020/0060687 A1 | 2/2020 | Hernández et al. |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0187942 A1 | 6/2020 | Wei |
| 2020/0205829 A1 | 7/2020 | Wei |
| 2020/0214733 A1 | 7/2020 | Drapeau |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |
| 2021/0137579 A1 | 5/2021 | Rafiee |

FOREIGN PATENT DOCUMENTS

| | | |
|---|---|---|
| EP | 0 558 031 B1 | 9/1993 |
| EP | 1 383 448 B1 | 6/2008 |
| EP | 1383448 B1 | 6/2008 |
| EP | 2760351 B1 | 5/2018 |
| FR | 2 705 556 A1 | 12/1994 |
| FR | 2 768 324 A1 | 3/1999 |

(56) References Cited

FOREIGN PATENT DOCUMENTS

| | | |
|---|---|---|
| FR | 2 768 325 B1 | 11/1999 |
| JP | 2016-508858 A | 3/2016 |
| WO | WO 91/01689 A1 | 2/1991 |
| WO | WO 92/12690 A1 | 8/1992 |
| WO | WO 94/018893 A1 | 9/1994 |
| WO | WO 95/08292 A1 | 3/1995 |
| WO | WO 96/32882 A1 | 10/1996 |
| WO | WO 97/27807 A1 | 8/1997 |
| WO | WO 98/07375 A1 | 2/1998 |
| WO | WO 99/07295 A1 | 2/1999 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | WO 2015/008286 A1 | 1/2015 |
| WO | WO 2015/057289 A1 | 4/2015 |
| WO | WO 2016/178722 A1 | 11/2016 |
| WO | WO 2018/093663 A1 | 5/2018 |
| WO | 2019058178 A1 | 3/2019 |
| WO | WO 2021/007324 A1 | 1/2021 |
| WO | 2021113785 A1 | 6/2021 |

OTHER PUBLICATIONS

U.S. Appl. No. 14/348,527 (U.S. Pat. No. 9,770,256) filed Mar. 28, 2014 (Sep. 26, 2017).
U.S. Appl. No. 15/714,692 (U.S. Pat. No. 10,624,664) filed Sep. 25, 2017 (Apr. 21, 2020).
U.S. Appl. No. 16/853,664 (US 2020/0261107) filed Apr. 20, 2020 (Aug. 20, 2020).
U.S. Appl. No. 17/744,218 (US 2022/0361907) filed May 13, 2022 (Nov. 17, 2022).
U.S. Appl. No. 14/348,527, filed Aug. 24, 2017 Issue Fee Payment.
U.S. Appl. No. 14/348,527, filed May 25, 2017 Notice of Allowance.
U.S. Appl. No. 14/348,527, filed Mar. 29, 2017 Response to Non-Final Office Action.
U.S. Appl. No. 14/348,527, filed Oct. 25, 2016 Non-Final Office Action.
U.S. Appl. No. 14/348,527, filed Jul. 22, 2016 Response to Restriction Requirement.
U.S. Appl. No. 14/348,527, filed May 25, 2016 Restriction Requirement.
U.S. Appl. No. 15/714,692, filed Mar. 13, 2020 Issue Fee Payment.
U.S. Appl. No. 15/714,692, filed Dec. 13, 2019 Notice of Allowance.
U.S. Appl. No. 15/714,692, filed Oct. 29, 2019 Response to Non-Final Office Action.
U.S. Appl. No. 15/714,692, filed May 31, 2019 Non-Final Office Action.
U.S. Appl. No. 16/853,664, filed Nov. 14, 2022 Notice of Allowance.
U.S. Appl. No. 16/853,664, filed Oct. 25, 2022 Response to Non-Final Office Action.
U.S. Appl. No. 16/853,664, filed Aug. 4, 2022 Non-Final Office Action.
Dang et al., "Surgical Revision After Percutaneous Mitral Valve Repair With a Clip: Initial Multicenter Experience," Ann Thorac Surg 80:2338-2342 (2005).
European Search Report dated Oct. 10, 2022 in Application No. EP 22173362.
Extended European Search Report dated May 19, 2021 in Application No. EP 18859611.
Extended European Search Report dated May 4, 2021 in Application No. EP 21161291.
International Search Report and Written Opinion for Application No. PCT/US2017/038309, dated Aug. 21, 2017.
International Search Report and Written Opinion mailed Jan. 8, 2019 in International Application No. PCT/IB2018/001188.
International Search Report mailed Mar. 11, 2013 in International Application No. PCT/US2012/058139.
Rose et al., "Late MitraClip Failure: Removal Technique for Leaflet-Sparing Mitral Valve Repair," Journal of Cardiac Surgery 27:543-545 (2012).

\* cited by examiner

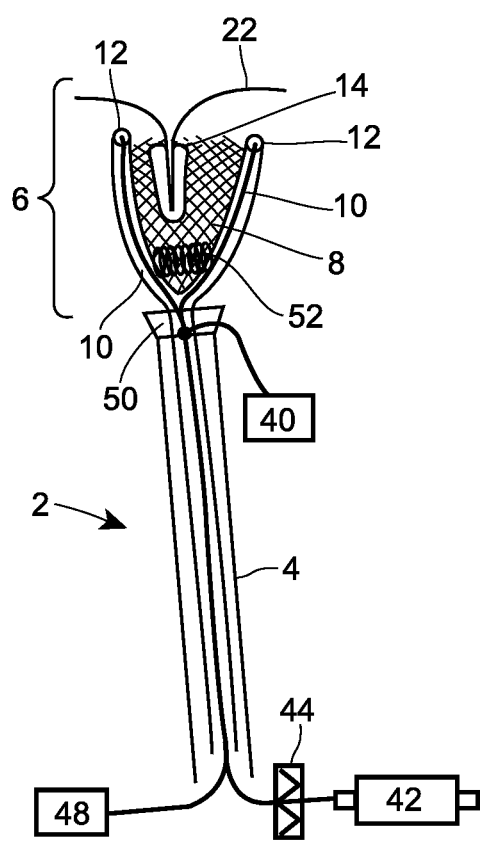
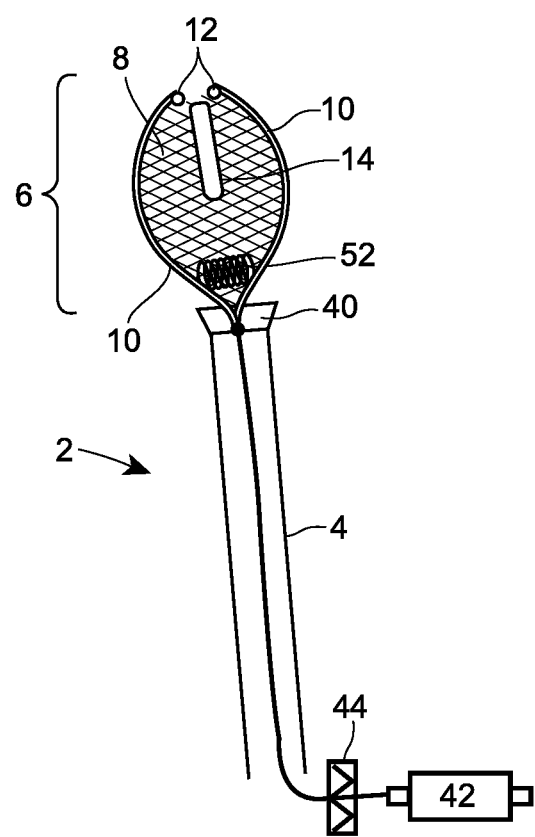
FIG. 1A
Prior Art
FIG. 1B
Prior Art

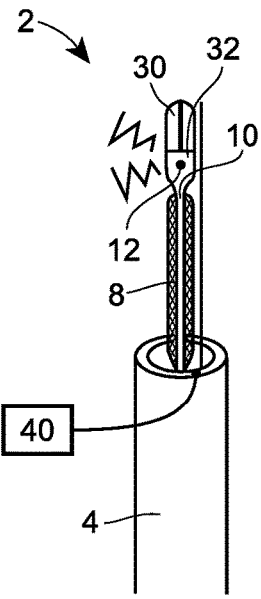 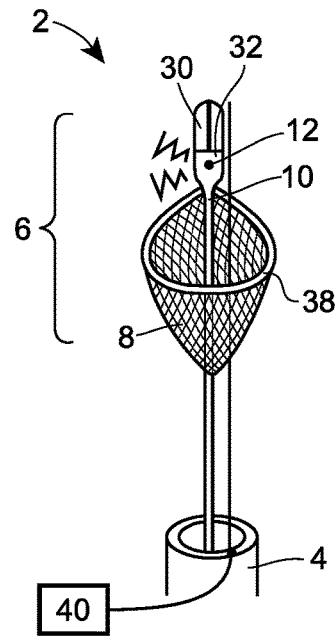 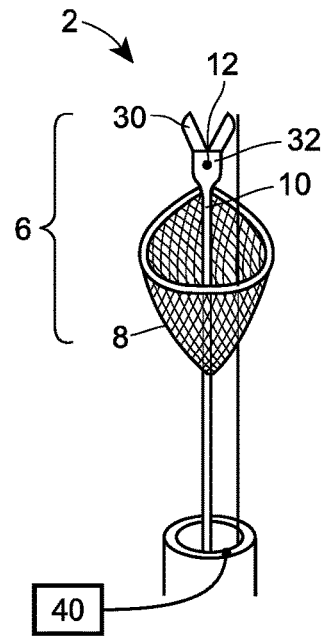
FIG. 2A  FIG. 2B  FIG. 2C
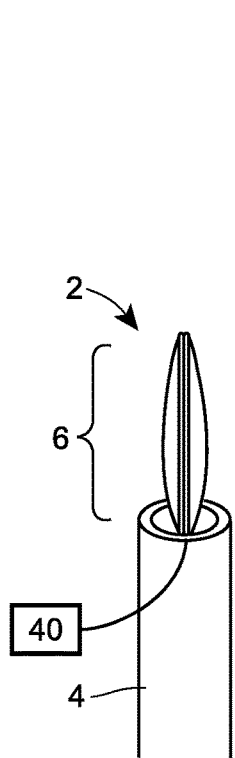 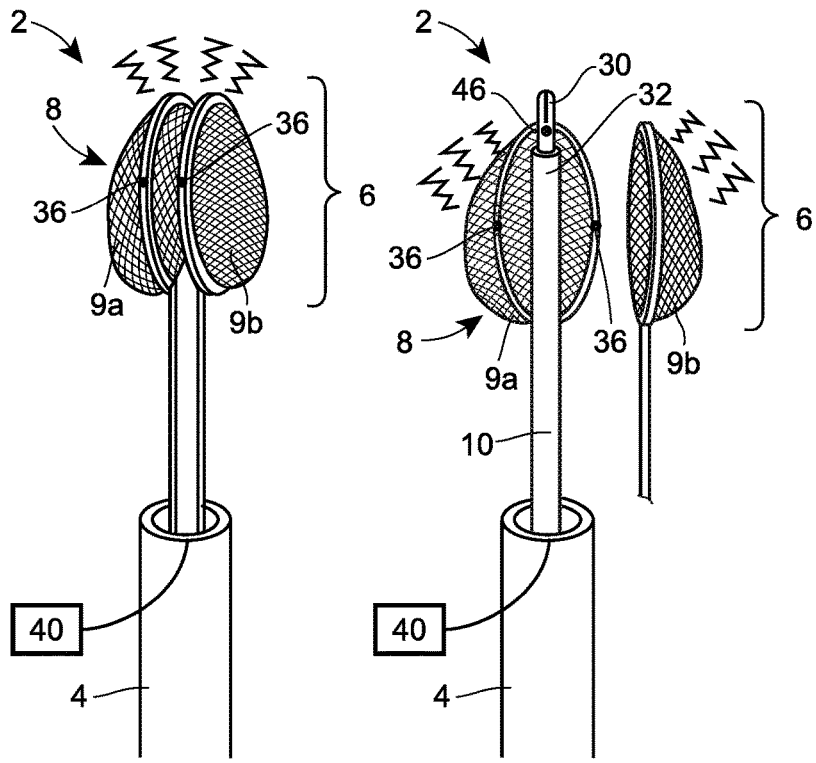
FIG. 3A  FIG. 3B  FIG. 3C

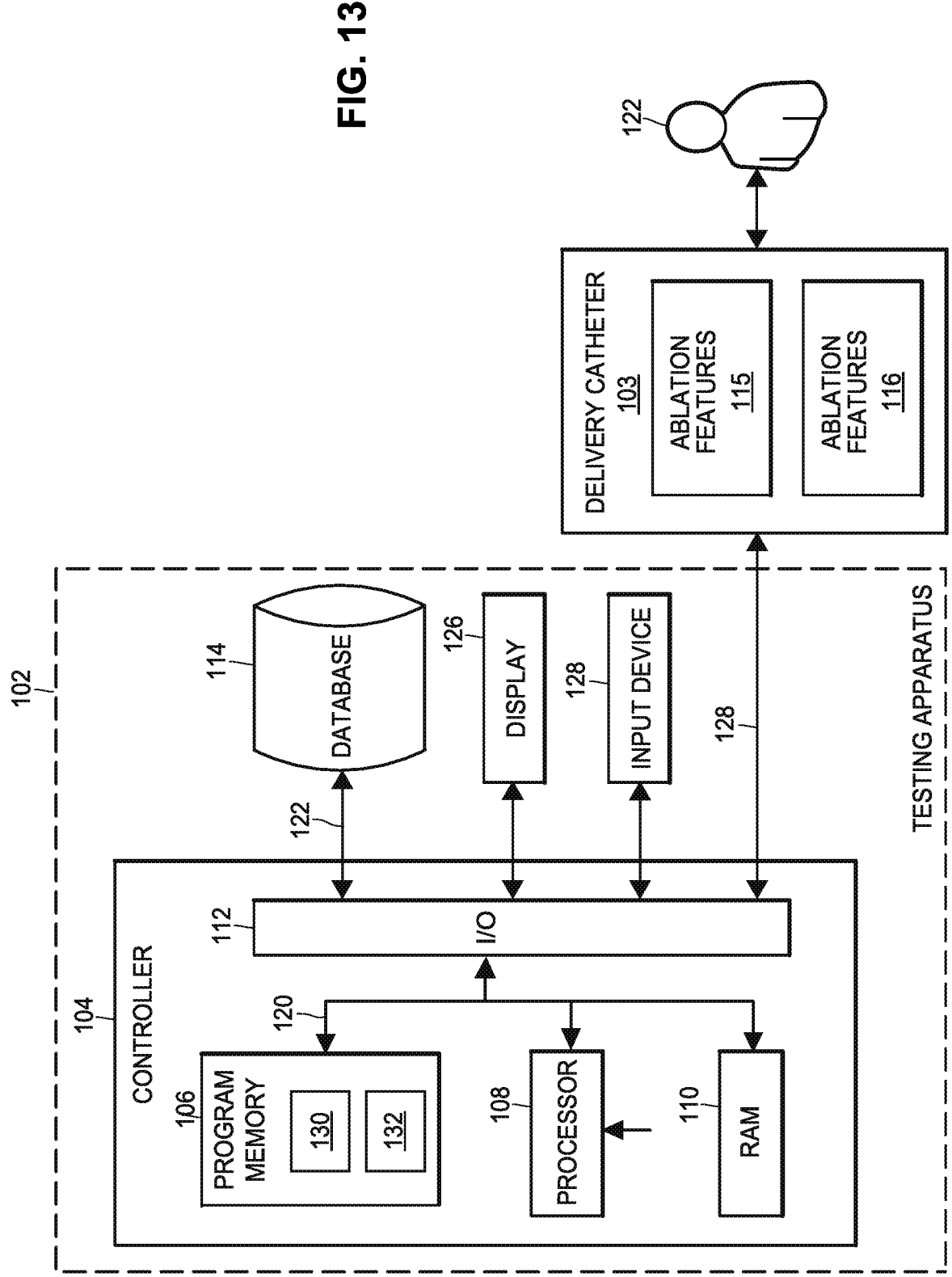

TRANSAPICAL REMOVAL DEVICE

CROSS-REFERENCE TO RELATED APPLICATION

This is a US national stage of International Application No. PCT/US17/38309, filed Jun. 20, 2017, which claims the priority of U.S. Provisional Patent Application No. 62/352,235, filed Jun. 20, 2016, and entitled "Transapical Removal Device"; the entire contents thereof are incorporated by reference herein.

FIELD OF THE DISCLOSURE

This disclosure relates generally to a transapical removal device, and more specifically, to a transapcial removal device for removal of a mitral valve clip or the anterior leaflet of the mitral valve.

BACKGROUND

Mitral valve regurgitation occurs when a heart's mitral valve does not close tightly, allowing some blood to leak backward through the mitral valve into the atrium rather than flowing through the aortic valve. Mitral valve regurgitation is present in approximately 1.7% of the adult population, and the incidence rises with advancing age such that more than 9% of adults 75 years of age and older have moderate or severe mitral valve regurgitation. Because blood cannot move through the heart or to the rest of the body as efficiently in people suffering from mitral valve regurgitation, symptoms include shortness of breath and fatigue, as well as heart murmur, heart palpitations, and swollen feet or ankles. Severe mitral valve regurgitation can lead to heart failure, atrial fibrillation, and pulmonary hypertension. If left untreated, the one year mortality rate for mitral valve regurgitation is 57%.

A variety of treatment options have been developed to treat mitral valve regurgitation, including medications, open-heart surgery, and catheter procedures. One catheter procedure involves clipping together mitral valve leaflets of the mitral valve in order to improve the function of the mitral valve. Under certain circumstances, such as an allergic reaction, dislodgement of the clip, or infection, removal of a mitral valve clip is necessary. Unfortunately, after mitral valve clip deployment, the mitral valve clip can only be removed surgically, closing the door for future percutaneous mitral valve replacement and causing elevated morbidity and mortality. Preferably, removal of the mitral valve clip could be achieved by a catheter procedure that would not require open-heart surgery. Additionally, some patients with mitral valve regurgitation undergo transcatheter mitral valve replacement and subsequently experience a left ventricular outflow tract (LVOT) obstruction. The anterior mitral leaflets have been identified as playing a considerable role in the etiology of LVOT obstructions in many patients. Preferably, any catheter procedure for removing a mitral valve clip could also ablate, remove or modify the anterior mitral valve leaflets as a first step to transcatheter mitral valve replacement in order to prevent future complications, such as an LVOT obstruction.

SUMMARY OF THE DISCLOSURE

The current disclosure is directed to multiple arrangements of a transapical removal device that can be deployed in a catheter procedure to capture for removal or alteration a mitral valve clip or heart tissue, such as the anterior leaflet of the mitral valve, as well as to methods of use of such a transapical removal device. The removal device includes a delivery catheter configured to be deployed near a mitral valve using a guide catheter. In some arrangements, the guide catheter can be used to deploy the delivery catheter.

The delivery catheter has a snare head at the distal end, which assumes a collapsed state during movement of the delivery catheter along the guide catheter and a deployed state for capturing a mitral valve clip or anterior leaflet. The snare head controller controls the transition of the snare head between the collapsed and deployed states. The snare head has a snare basket for at least partially surrounding a pre-positioned mitral valve clip or the anterior leaflet. The snare basket may be made of, for example, medical-grade plastic, medical-grade metal, or both. The snare basket may be made of a shape memory material, such as nitinol, that assists in the transition from the collapsed state to the deployed state. In some arrangements, the snare head may comprise a spring that is compressed when the snare head is in the collapsed state and at rest when the snare head is in the deployed state, the spring configured to be compressed within the snare basket unless the snare basket is in the deployed state. A retraction funnel may be provided at a proximal end of the delivery catheter in order to forcibly return the snare head to the collapsed state from the deployed state. In some arrangements, magnets may be provided on the snare basket to facilitate closing the snare basket around the pre-positioned mitral valve clip or the anterior leaflet. In other arrangements, the snare basket may comprise a cord for cinching the snare basket around the pre-positioned mitral valve clip or the anterior leaflet.

In some arrangements, the snare basket may be a single-part basket having an oval shape. In other arrangements, the snare basket may be a two-part basket having a first basket side and a second basket side. The two-part basket may have a closed state, in which the first basket side and the second basket side are arranged to secure a mitral valve clip, tissue, or another element between them, and an open state, in which the first and second basket sides are separated from one another.

The snare head also has one or more ablation delivery catheters configured to ablate tissue surrounding the pre-positioned mitral valve clip or anterior leaflet. In some arrangements within the scope of the present disclosure, each ablation delivery catheter comprises an electrode for supplying radiofrequency energy to ablate tissue adjacent the mitral valve clip or anterior leaflet to allow for removal of the mitral valve clip or removal or alteration of the anterior leaflet. An electrical source, such as a battery, may be provided that is in communication with the electrodes, and a switch may alternately permit and cease to permit electrical current to flow from the electrical source to the electrodes. The switch may be controlled remotely. In other arrangements within the scope of the present disclosure, each ablation delivery catheter includes an optical fiber positioned to deliver a laser ablation signal to ablate tissue adjacent the mitral valve clip or anterior leaflet to allow for removal of the mitral valve clip or removal or alteration of the anterior leaflet. The transapical removal device may include an ablation source, such as a radiofrequency source, a laser source, or a cryo-thermal source. When the ablation source is a radiofrequency source, the radiofrequency signal may be in the range of 250-500 kHz. The snare head is controlled by a snare head controller connected at a proximal end of the delivery catheter. The snare head controller is configured to control the position and/or size of the snare basket during the deployed state and to control ablation source delivery to the tissue during the deployed state.

In some arrangements within the scope of the present disclosure, the transapical removal device comprises a grasping tool movable between a closed and open state and controlled by the snare head controller. The grasping tool is configured to allow manipulation of tissue or a mitral valve clip as needed. The grasping tool may be controllably movable by the snare head controller between a position inside a tube and a position outside the tube, and the snare head controller may control the movement of the grasping tool between the positions. The tube may be connected with or integral with the snare head.

In some arrangements within the scope of the present disclosure, the removal device includes a deployment mechanism for deploying a transcatheter valve into the mitral valve to replace a removed mitral valve clip. The deployment mechanism may comprise a delivery catheter, which contains the transcatheter valve and is configured to deliver, in a valve replacement mode, the transcatheter valve into the mitral valve to replace the removed mitral valve.

BRIEF DESCRIPTION OF THE DRAWINGS

FIG. 1A illustrates a top view of a first arrangement of a transapical removal device of the present disclosure with the snare head in a deployed state.

FIG. 1B illustrates a top view of the first arrangement of the transapical removal device of FIG. 1A with the snare head in a collapsed state.

FIG. 2A illustrates an isometric side view of a second arrangement of a transapical removal device of the present disclosure with the snare head in a collapsed state wand a grasping tool of the snare head in a closed state.

FIG. 2B illustrates an isometric side view of the second arrangement of the transapical removal device of FIG. 2A with the snare head in a deployed state and the grasping tool of the snare head in a closed state.

FIG. 2C illustrates an isometric side view of the second arrangement of the transapical removal device of FIGS. 2A and 2B with the snare head in a deployed state and the grasping tool of the snare head in an open state.

FIG. 3A illustrates an isometric side view of a third arrangement of a transapical removal device of the present disclosure with a snare head in a collapsed state.

FIG. 3B illustrates an isometric side view of the third arrangement of the transapical transapical removal device of FIG. 3A with the snare head in a deployed state and the snare basket of the snare head in a closed state.

FIG. 3C illustrates an isometric side view of the third arrangement of the transapical removal device of FIGS. 3A and 3B with the snare head in a deployed state, the snare basket of the snare head in an open state, and a retractable grasping tool of the snare head in a closed state.

FIG. 13 is an example block diagram 100 illustrating the various components used in implementing an example arrangement of a method of using a transapical removal device 102.

DETAILED DESCRIPTION

Figure 4:
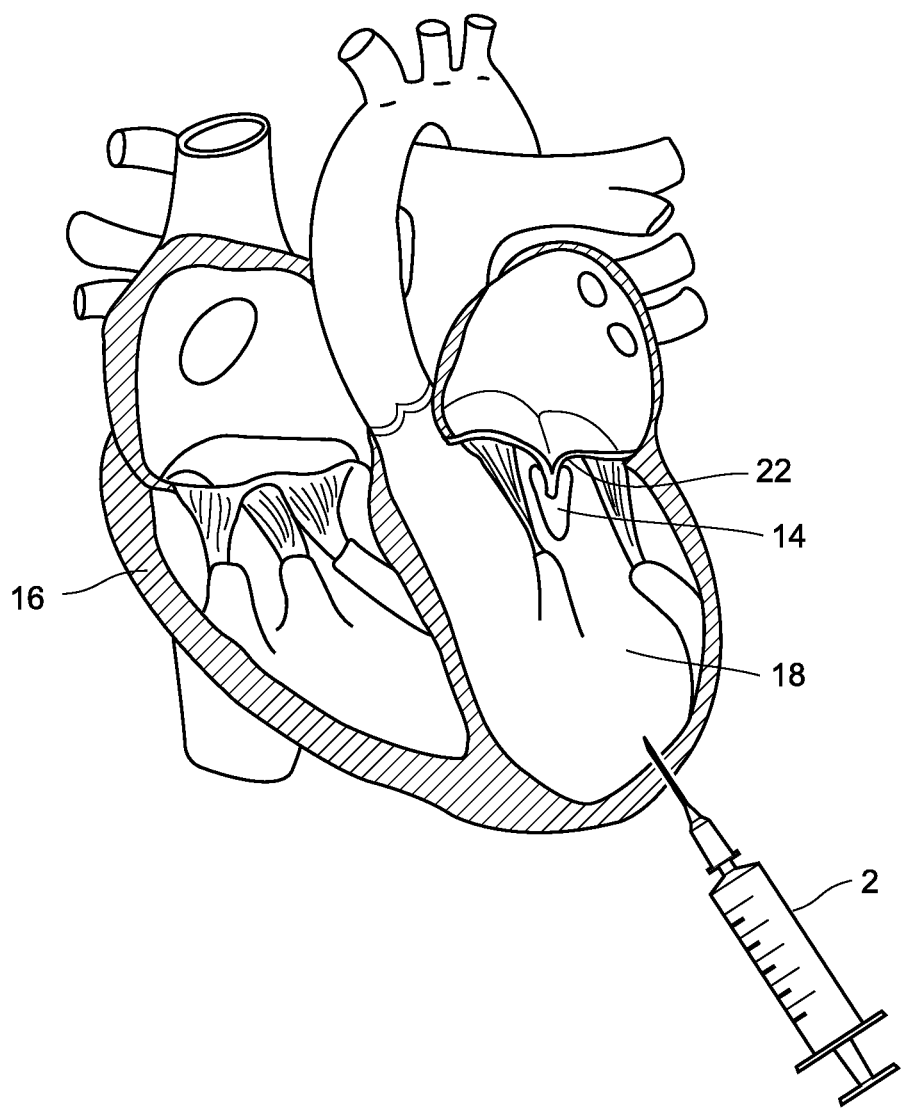
FIG. 4 illustrates a heart of a patient having a mitral clip at the mitral valve, wherein the transapical removal device of the present disclosure is being used to puncture the left ventricle of the heart.

FIGS. 1A and 1B illustrate a first arrangement of a transapical removal device 2 of the present disclosure. The transapical removal device 2 includes a delivery catheter 4, a snare head 6, a snare basket 8, a spring 52, and ablation delivery catheters 10 with electrodes 12. An electrical source 42 and an ablation source 48 are in communication with the electrodes 12, and a switch 44 alternately permits and ceases to permit electrical current from the electrical source 42 to flow to the electrodes 12. In FIG. 1A, the snare head 6 and snare basket 8 are in a deployed state outside of the delivery catheter 4, and a mitral clip 14 is surrounded by the sides of the snare basket 8. The electrodes 12 of the ablation delivery catheters 10 are aligned with tissue of the heart that is to be ablated in order for the mitral clip 14 to be captured. For example, such tissue may be ablated when a control signal is provide to activate the ablation source 48 to provide an ablation signal, such as a radiofrequency signal, through the catheter 10 to ablate tissue of the mitral valve. FIG. 1B depicts the transapical removal device 2 after ablation has occurred and the mitral clip 14 has been captured by the snare basket 8. The snare head 6 is now in a collapsed configuration and can be removed from the heart, e.g., by being retracted through the delivery catheter 4. The transition of the snare head 6 between the collapsed state and the deployed state is controlled by a snare head controller 40 connected at a proximal end of the delivery catheter 4. A retraction funnel 40 is provided to forcibly return the snare head to a collapsed state. The spring 52 is compressed when the snare head 6 is in the collapsed state and at rest when the snare head 6 is in the deployed state. For this catheter-based removal technique, the snare head 6 may apply pressure to the captured mitral valve clip 14 to collapse the clip down to a size or close to that of its initial size prior to deployment. This will allow the clip 14 to be removed through the catheter 4 more easily. It is noted that in some instances a slightly larger diameter delivery catheter 4 may be desired (in comparison to the original mitral valve clip delivery catheter) to compensate for tissue attached to the mitral valve clip 14 and ablated by the delivery catheters 10.

FIGS. 2A-2C illustrate a second arrangement of a transapical removal device 2 of the present disclosure. In addition to the elements discussed with respect to FIGS. 1A and 1B, the second arrangement of the transapcial removal device 2 includes a grasping tool 30 controllable by the snare head controller 40. The grasping tool 30 is movable between a closed state (shown in FIGS. 2A and 2B) and an open state (shown in FIG. 2C) and is configured to allow manipulation of tissue or the mitral valve clip as needed. The grasping tool 30 may be retractable such that it is controllably movable between a position inside a tube 32 and a position outside the tube 32. The snare basket 8 of the transapical removal device 2 depicted in FIGS. 2A-2C is closed by pulling on a cord 38, optionally using the grasping tool 30, in order to cinch the snare basket 8 closed.

FIGS. 3A-3C illustrate a third arrangement of a transapical removal device 2 of the present disclosure. The third arrangement of the transapical removal device 2 includes the elements disclosed with respect to the first and second arrangements. In the third arrangement of the transapical removal device 2, the snare head 6 has a two-part snare basket 8 having a first basket side 9a and a second basket side 9b. The third arrangement of the transapical removal device 2 allows the transapical removal device 2 to move between a collapsed state (shown in FIG. 3A), a deployed and closed state in which the first basket side 9a and the second basket side 9b are arranged to secure a mitral valve clip, tissue, or another element between them (shown in FIG. 3B), and a deployed and open state in which the first basket side 9a and the second basket side 9b are separated from one another, such as by being rotated to be at an angle relative to each other (shown in FIG. 3C). The first basket side 9a and the second basket side 9b have magnets 36 disposed on them that attract one another and thus facilitate moving the snare basket 8 to a closed state. In the third arrangement, ablation of heart tissue is achieved by an optical fiber 46.

Figure 5:
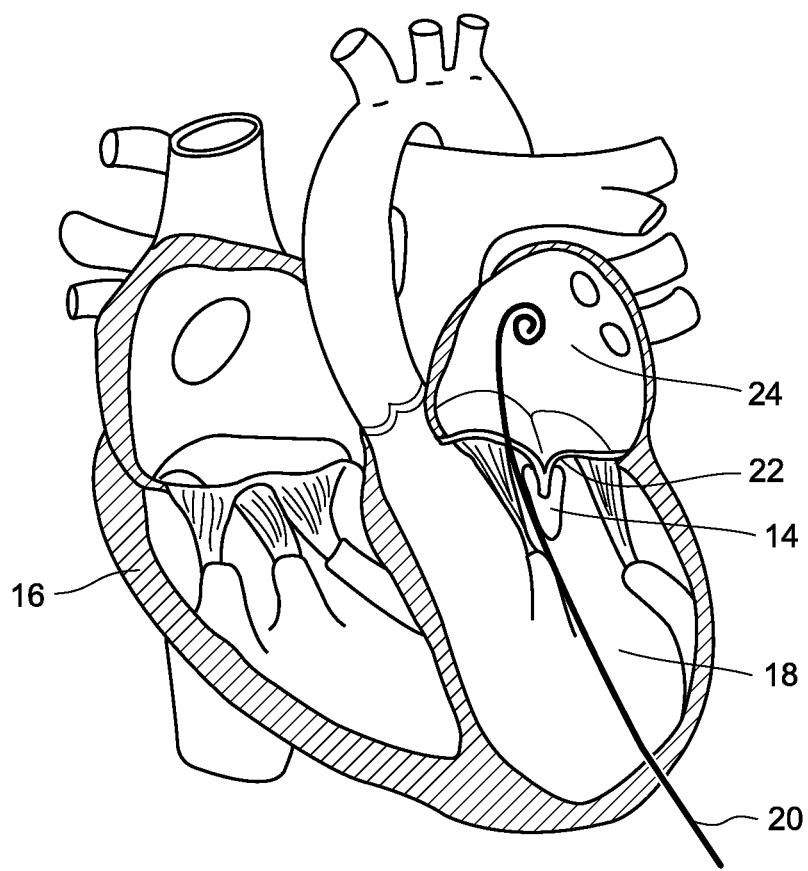
FIG. 5 illustrates the heart of the patient depicted in FIG. 4, wherein a guide wire of the transapical removal device of the present disclosure is being inserted through the puncture in the left ventricle, into the left ventricle, and up into the left atrium.
Figure 6:
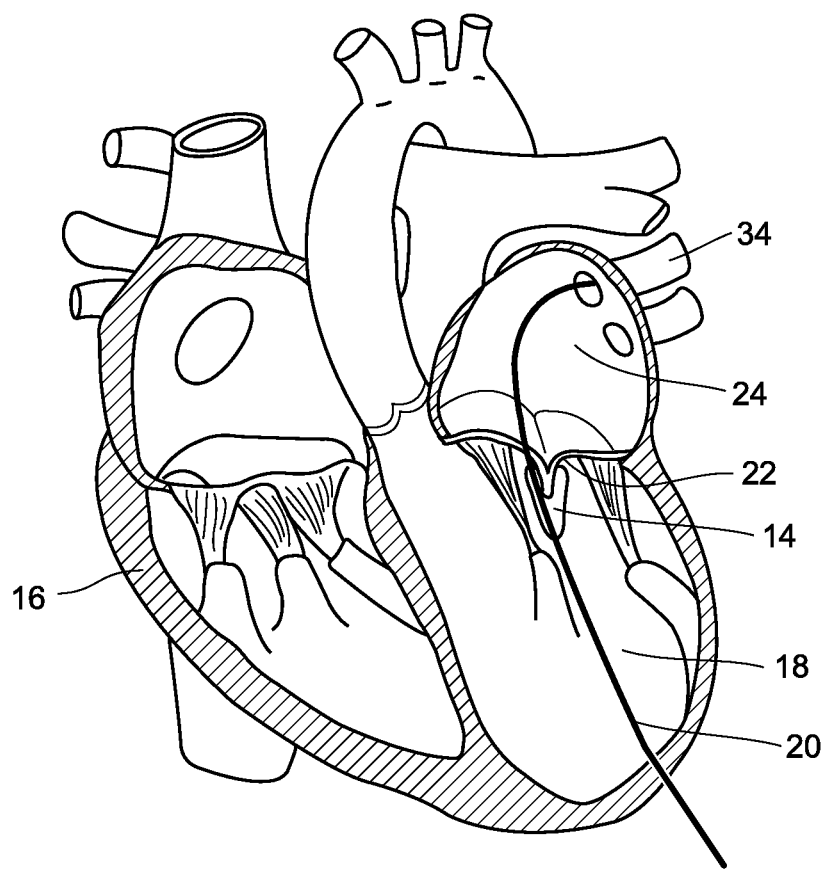
FIG. 6 illustrates the heart of the patient depicted in FIGS. 4 and 5, wherein a guide wire of the transapcial removal device of the present disclosure is being inserted into a pulmonary vein.
Figure 7:
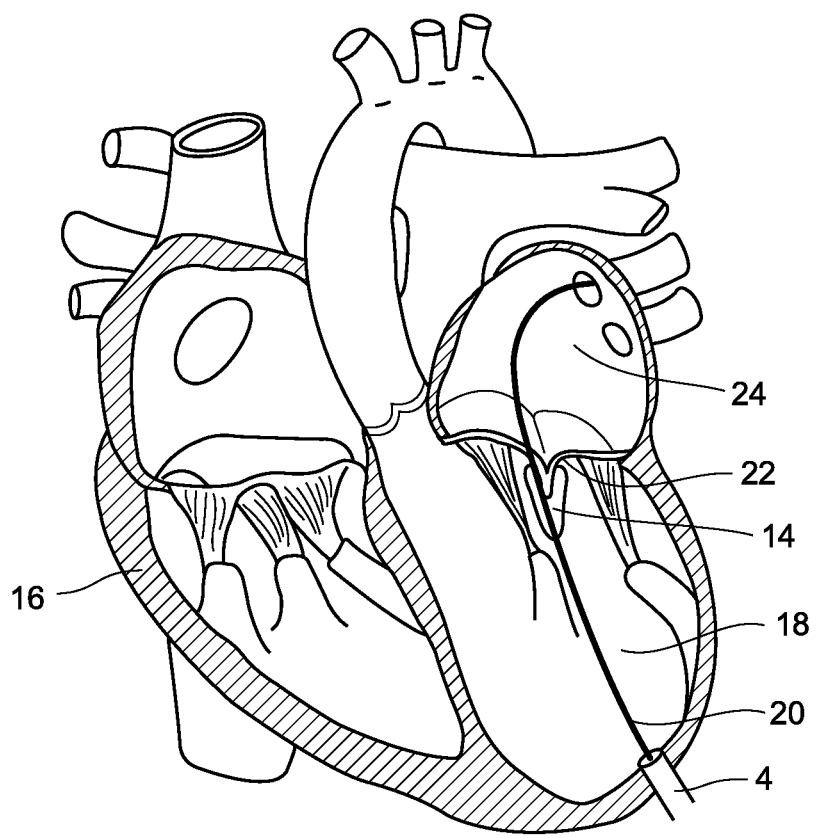
FIG. 7 illustrates the heart of the patient depicted in FIGS. 4-6, wherein a delivery catheter of the transapical removal device of the present disclosure is inserted into the left ventricle over the guide wire.
Figure 8:
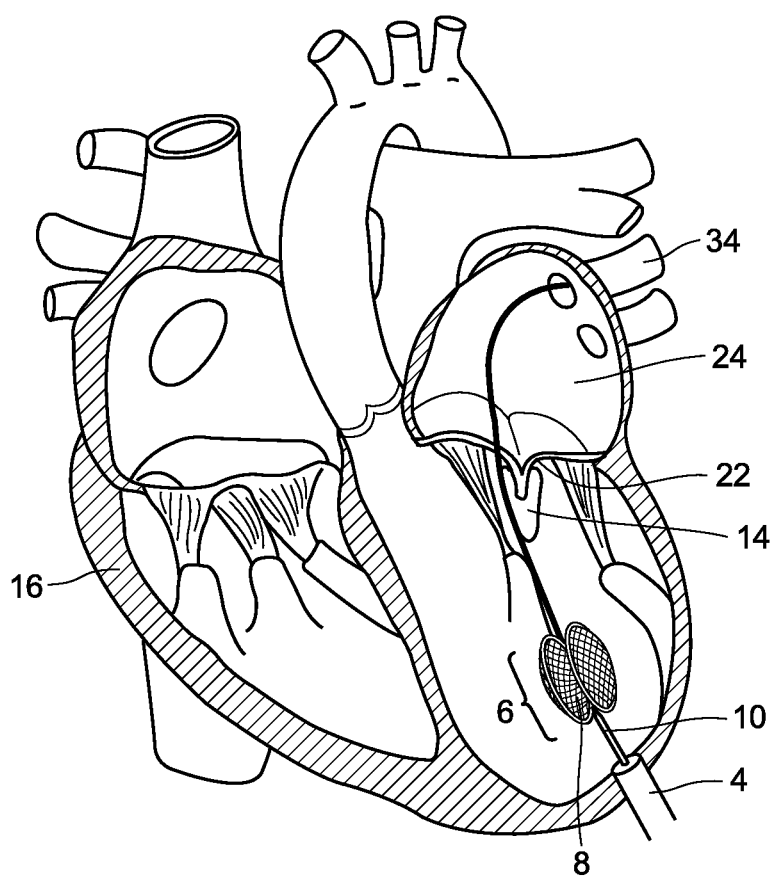
FIG. 8 illustrates the heart of the patient depicted in FIGS. 4-7, wherein a snare head is deployed from the delivery catheter.
Figure 9:
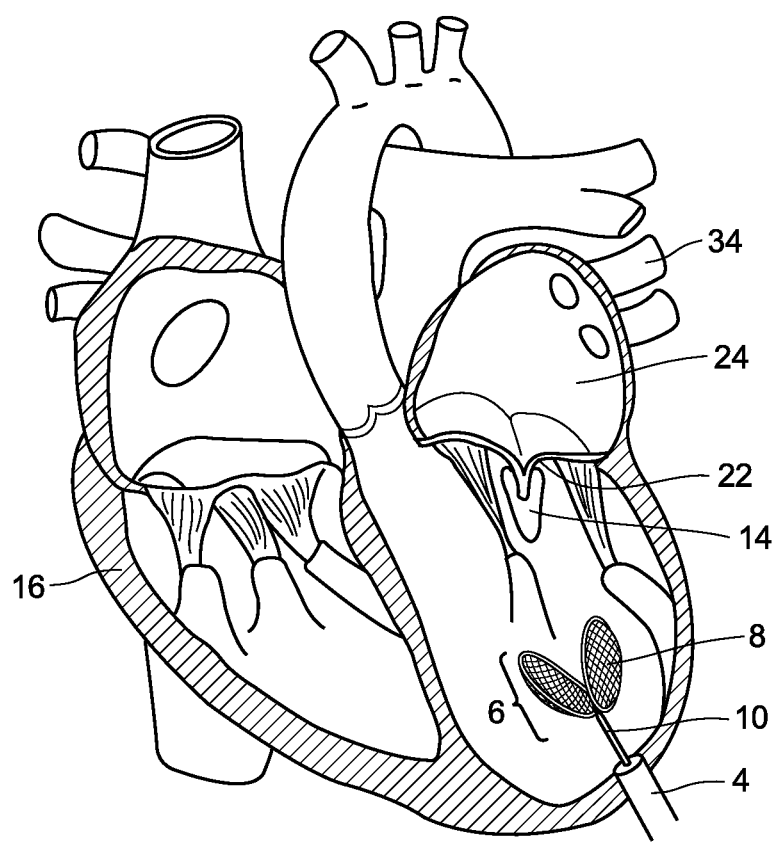
FIG. 9 illustrates the heart of the patient depicted in FIGS. 4-8, wherein the snare head is opened so that it can surround the mitral clip.
Figure 10:
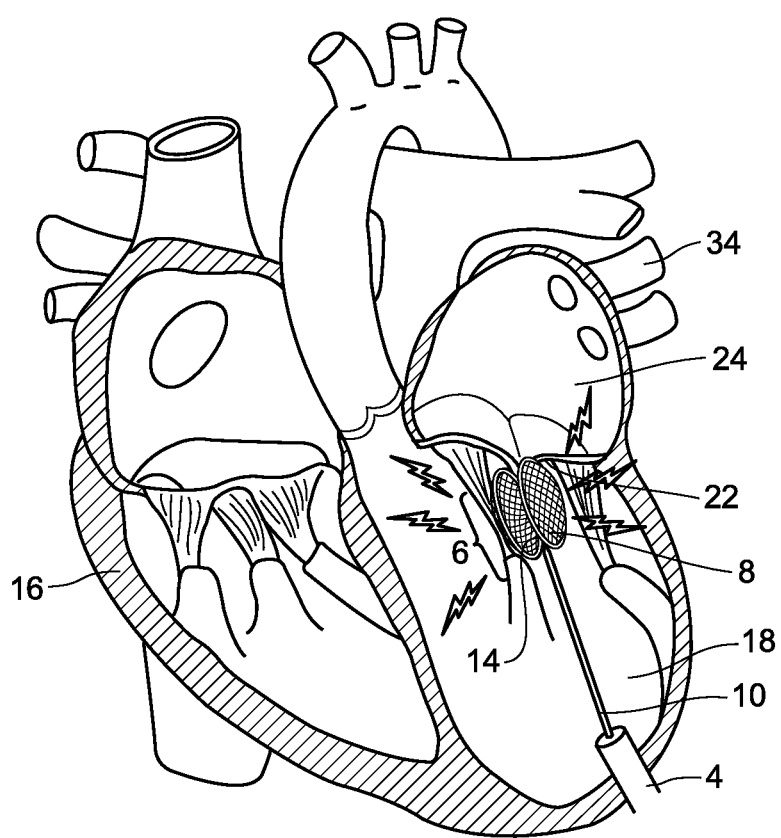
FIG. 10 illustrates the heart of the patient depicted in FIGS. 4-9, wherein the snare head is closed around the mitral clip, the tissue surrounding the mitral clip is ablated, and the mitral clip is captured in the snare head.

FIGS. 4-12 depict a transapical method of removing a mitral valve clip 14. This method could also be used to remove or alter an anterior leaflet of the mitral valve. In FIG. 4, a mitral valve clip 14 that has been pre-positioned on the mitral valve 22 to bind at least a portion of the mitral valve is depicted in a heart 16 of a patient. The transapical removal device 2 is used to puncture the left ventricle 18 of the heart 16. As shown in FIG. 5, a guide catheter 20 is then inserted into the left ventricle, through the mitral valve 22, and into the left atrium 24. As shown in FIG. 6, the guide catheter 20 may be inserted into a pulmonary vein 34. As shown in FIG. 7, using the guide catheter 20, the delivery catheter 4 is inserted into the left ventricle 18. As shown in FIG. 8, the snare head 6 is deployed from a collapsed state that allowed it to move through the delivery catheter 4 to a deployed state that allows it to capture the mitral valve clip 14. A snare head controller (not pictured) controls the transition of the snare head between the collapsed state and the deployed state. As shown in FIG. 9, the snare head 6 has a snare basket 8 that opens to at least partially surround the pre-positioned mitral valve clip 14. The snare basket may include medical-grade plastic, medical-grade metal, or both. In some arrangements within the scope of the present disclosure, the snare head 6 may be made from a shape memory material such as nitinol in order to assist with deployment of the snare head 6. In other arrangements within the scope of the present disclosure, such as that shown in FIGS. 1A and 1B, the snare head 6 may include a spring that is compressed when the snare head 6 is in the collapsed state and at rest when the snare head 6 is in the deployed state, the spring configured to be compressed within the snare basket 8 unless the snare basket 8 is in the deployed state. As shown in FIG. 10, the snare basket 8 then closes around the mitral valve clip 14. In some arrangements, the snare head 6 may include magnets 36 (shown in FIGS. 3B and 3C) that cause the snare head basket 8 to close.

Once the snare basket is closed around the mitral valve clip 14, an ablation signal is provided to the ablation delivery catheters 10 and delivered to the tissue surrounding the mitral valve clip 14. In some arrangements within the scope of the present disclosure, the ablation delivery catheters 10 each have an electrode 12 provided on a distal end for supplying radiofrequency energy to ablate tissue. The radiofrequency signal may be in the range of 250-500 kHz. An electrical source 42 (shown in FIGS. 1A and 1B) such as a battery, can be in communication with the electrodes 12, and a switch 44 may be provided that alternately permits and ceases to permit electrical current to flow from the electrical source to the electrodes. The switch may be controlled remotely. In other arrangements within the scope of the present disclosure, an optical fiber 46 (shown in FIG. 3C) is positioned at a distal end of each ablation delivery catheter 10 to deliver a laser ablation signal to ablate tissue adjacent the mitral valve clip 14. In other arrangements, the ablation source may be a cryo-thermal source.

Figure 11:
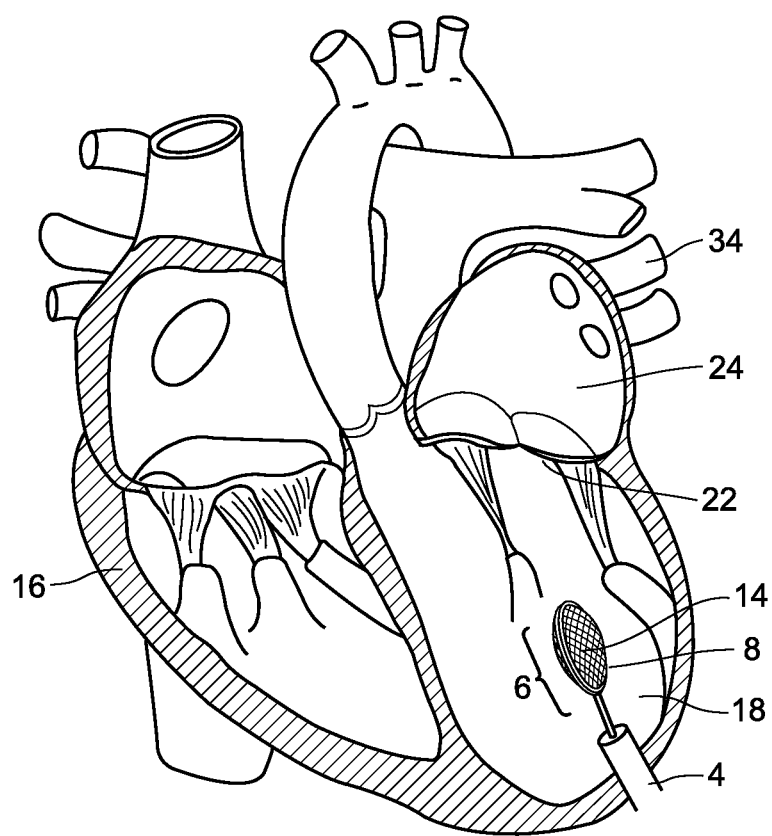
FIG. 11 illustrates the heart of the patient depicted in FIGS. 4-10, wherein the snare head is in a collapsed state after capturing the mitral clip.
Figure 12:
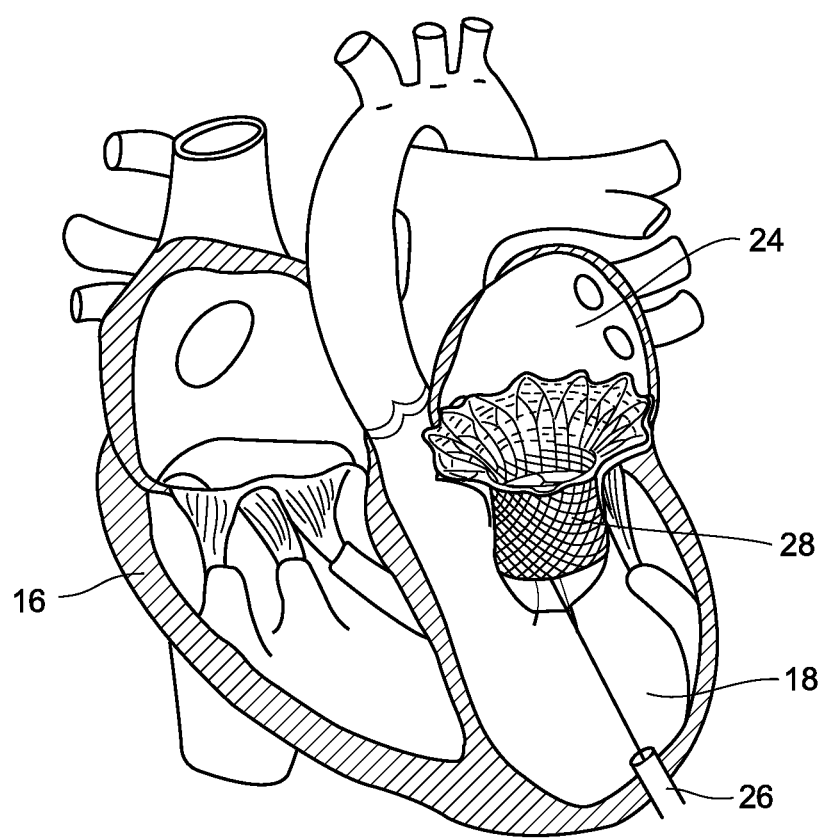
FIG. 12 illustrates the heart of the patient depicted in FIGS.4-11, wherein a new transcatheter valve is deployed into the mitral valve through the delivery catheter.

The snare head controller controls the position and/or size of the snare basket 8 during the deployed state and also controls ablation source delivery to the tissue during the deployed state. The mitral valve clip 14 is then captured by the snare basket 8 of the snare head 6. As shown in FIG. 11, the snare head 6 assumes a collapsed state and is retracted into the delivery catheter 4. In some arrangements within the scope of the present disclosure, a retraction funnel (shown in FIGS. 1A and 1B) may be provided at a proximal end of the delivery catheter 4 to help forcibly return the snare head 6 to the collapsed state from the deployed state. In order to provide a functional mitral valve 22, a new transcatheter valve 28 may be deployed by a deployment mechanism 26, which includes the delivery catheter 4 in the arrangement depicted in FIG. 12.

Although the method of using a transapical removal device 2 depicted in FIGS. 4-12 is directed to removal of a mitral valve clip 14, the transapical removal device 2 could be used for other purposes, such as to remove or alter the anterior leaflet. A person having skill in the art would recognize that substantially the same steps as discussed above could be used for such purposes. Although the snare basket 8 is depicted as having a two-part snare basket in FIGS. 4-12, a single-part basket or a multi-part basket having more than two sides may be used. Further, the snare basket 8 may be configured in a variety of shapes may. For example, the snare basket 8 may be open-ended at its distal and proximal ends for slidable removal of the captured tissue and/or clip, once the assembly is fully extracted from the subject. In other examples, the snare basket 8 may be continuous or otherwise sealed at the distal and proximal ends. In some examples, the snare basket 8 may have a flat configuration that facilitates removal or alteration of the anterior leaflet. In yet other examples, the ablation delivery catheters 10 may be secured to the snare basket 8 in a way that allows ablation of only a portion of an anterior leaflet, such as the center portion.

FIG. 13 is an example block diagram 100 illustrating the various components used in implementing an example arrangement of a method of using a transapical removal device as discussed herein. A transapical removal device may be inserted into a patient 122 via a delivery catheter 103 that may include ablation features 115 and sensors 116. The removal device may be controlled by a control system 102 having a snare head controller 104 operatively connected to various elements of the system 102. The control system 102 may be a standalone transapical device removal system, such as a portable machine at a point of care position. In other examples, the control system 102 may be implemented into existing control systems, such as an existing ablation control system, having an ablation pump, a catheter sensor/switching control system, etc. While not shown, the control system 102 may include mechanical controls, such as foot controls and hand controls for providing full or partial mechanical operation of catheter delivery, snare head deployment, and ablation features. It will be appreciated that some portion of the control system 102, whether electronic and/or mechanical portions, may be distributed into a control handle for the delivery catheter of the removal device, for snare head, sensor, and/or catheter control.

In the illustrated example, the control system 102 includes a database 114 (via a link 122 connected to an input/output (I/O) circuit 112) for storing collect data, such as historical data from the controller 104 and/or from external data sources, such as historical data collected from other medical devices and medical databases. That is, it should be noted that, while not shown, additional databases may be linked to the snare head controller 104 in a known manner.

The snare head controller 104 includes a program memory 106, the processor 108 (may be called a microcontroller or a microprocessor), a random-access memory (RAM) 110, and the input/output (I/O) circuit 112, all of which are interconnected via an address/data bus 120. It should be appreciated that although only one microprocessor 108 is shown, the snare head controller 104 may include multiple microprocessors 108. Similarly, the memory of the controller 104 may include multiple RAMs 110 and multiple program memories 106. Although the I/O circuit 112 is shown as a single block, it should be appreciated that the I/O circuit 112 may include a number of different types of I/O circuits. The RAM(s) 110 and the program memories 106 may be implemented as semiconductor memories, magnetically readable memories, and/or optically readable memories, for example. A link 124 may operatively connect the controller 104 to the sensors 116 through the I/O circuit 112.

The program memory 106 and/or the RAM 110 may store various applications (i.e., machine readable instructions) for execution by the microprocessor 108. For example, an operating system 130 may generally control the operation of the control system 102 and provide a user interface to the control system 102 to implement the removal processes described herein. The program memory 106 and/or the RAM 110 may also store a variety of subroutines 132 for accessing specific functions of the testing apparatus 102. By way of example, and without limitation, the subroutines 132 may include, among other things: a subroutine for controlling ablation of mitral valve tissue, a subroutine for controlling activation of a snare head from a first collapsed state for delivery to the mitral value, to a deployed state for snaring the mitral valve clip, and then to a second collapsed state for removing the capture mitral valve clip, as well as other subroutines, for example, implementing software keyboard functionality, interfacing with other hardware in the computer system 102, etc. The program memory 106 and/or the RAM 110 may further store data related to the configuration and/or operation of the transapical removal device, and/or related to the operation of one or more subroutines 132. In addition to the controller 104, the control system 102 may include other hardware resources.

The control system 102 may also include various types of input/output hardware such as a visual display 126 and input device(s) 128 (e.g., keypad, keyboard, etc.). In an arrangement, the display 126 is touch-sensitive, and may cooperate with a software keyboard routine as one of the software routines 132 to accept user input. It may be advantageous for the testing apparatus to communicate with broader medical analysis networks or medical treatment networks (not shown) through any of a number of known networking devices and techniques (e.g., through a commuter network such as a hospital or clinic intranet, the Internet, etc.). For example, the control system 102 may be connected to a medical records database, hospital management processing system, health care professional terminals (e.g., doctor stations, nurse stations), patient monitoring systems, automated drug delivery systems. Accordingly, the disclosed arrangements may be used as part of an automated closed loop system or as part of a decision assist system.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain arrangements are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example arrangements, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various arrangements, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering arrangements in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In arrangements in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example arrangements, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example arrangements, the processor or processors may be located in a single location (e.g., within a home environment, an office environment or as a server farm), while in other arrangements the processors may be distributed across a number of locations.

The performance of certain of the operations may be distributed among the one or more processors, not only residing within a single machine, but deployed across a number of machines. In some example arrangements, the one or more processors or processor-implemented modules may be located in a single geographic location (e.g., within a home environment, an office environment, or a server farm). In other example arrangements, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Some arrangements may be described using the expression "coupled" and "connected" along with their derivatives. For example, some arrangements may be described using the term "coupled" to indicate that two or more elements are in direct physical or electrical contact. The term "coupled," however, may also mean that two or more elements are not in direct contact with each other, but yet still co-operate or interact with each other. The arrangements are not limited This detailed description is to be construed as examples and does not describe every possible arrangement, as describing every possible arrangement would be impractical, if not impossible. One could implement numerous alternate arrangements, using either current technology or technology developed after the filing date of this application.

As used herein any reference to "one arrangement" or "an arrangement" means that a particular element, feature, structure, or characteristic described in connection with the arrangement is included in at least one arrangement. The appearances of the phrase "in one arrangement" in various places in the specification are not necessarily all referring to the same arrangement.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the arrangements herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed arrangements without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:
1. A transapical removal device comprising:
   a delivery catheter configured to be deployed near a mitral valve using a guide catheter;
   a snare head at a distal end of the delivery catheter, the snare head having (i) a collapsed state for movement of the delivery catheter through the guide catheter and (ii)

a deployed state for capturing a mitral valve clip that has been pre-positioned on a mitral valve leaflet; and a snare head controller connected at a proximal end of the delivery catheter and configured to control transition of the snare head between the collapsed state and the deployed state;

wherein the snare head includes a removal tool comprising a snare basket and one or more ablation delivery catheters secured to the snare basket, the snare basket configured to at least partially surround the pre-positioned mitral valve clip, and the one or more ablation delivery catheters configured to ablate the mitral valve leaflet for removal of the pre-positioned mitral valve clip from the mitral valve leaflet, and a grasping tool having opposed first and second members moveable away from and toward each other between an open state and closed state, respectively, and configured to grasp and manipulate the pre-positioned mitral valve clip while the snare basket at least partially surrounds the pre-positioned mitral valve clip; and wherein the snare head controller is configured to (x) control the position and/or size of the snare basket during the deployed state, (y) move the grasping tool between the closed state and the open state, and/or (z) control ablation delivery to the mitral valve leaflet through the one or more ablation delivery catheters, wherein the snare basket defines an interior space, and the grasping tool is positionable at least partially within the interior space of the basket, and wherein magnets are provided on the snare basket to facilitate closing the snare basket around the mitral valve clip.

2. The transapical removal device of claim 1, further comprising the guide catheter used to deploy the delivery catheter.

3. The transapical removal device of claim 1, wherein a distal end of each of the one or more ablation delivery catheters comprises an electrode for supplying radio frequency energy to ablate tissue adjacent the mitral valve clip to allow for removal of the mitral valve clip.

4. The transapical removal device of claim 3, further comprising:

an electrical source in electrical communication with at least one electrode; and a switch, the switch alternately permitting and ceasing to permit electrical current from the electrical source to flow to the at least one electrode.

5. The transapical removal device of claim 4, wherein the switch is controlled remotely.

6. The transapical removal device of claim 4, wherein the electrical source is a battery.

7. The transapical removal device of claim 1, wherein a distal end of each of the one or more ablation delivery catheters comprises an optical fiber positioned to deliver a laser ablation signal to ablate tissue adjacent the mitral valve clip to allow for removal of the mitral valve clip.

8. The transapical removal device of claim 1, further comprising an ablation source in communication with the one or more ablation delivery catheters, wherein the ablation source is one of a radiofrequency source, laser source, and cryo-thermal source.

9. The transapical removal device of claim 8, wherein the ablation source is a radiofrequency signal in the range of 250-500 kHz.

10. The transapical removal device of claim 1, wherein the snare head comprises shape memory material.

11. The transapical removal device of claim 10, wherein the shape memory material is nitinol.

12. The transapical removal device of claim 1, further comprising a retraction funnel at a proximal end of the delivery catheter configured to return the snare head to the collapsed state from the deployed state.

13. The transapical removal device of claim 1, wherein the snare head comprises a spring that is compressed when the snare head is in the collapsed state and at rest when the snare head is in the deployed state.

14. The transapical removal device of claim 1, wherein the snare basket comprises a first basket side and a second basket side.

15. The transapical removal device of Claim 1, wherein the snare basket comprises a cord for cinching the snare basket around the mitral valve clip.

16. The transapical removal device of Claim 1, wherein the grasping tool is controllably movable by the snare head controller between a position inside a tube and a position outside the tube.

* * * * *